(12) United States Patent
Sander et al.

(10) Patent No.: US 10,646,613 B2
(45) Date of Patent: *May 12, 2020

(54) WOUND SPRAY

(75) Inventors: Michael Sander, Werther (DE); Harald Potzschke, Wiesbaden (DE)

(73) Assignee: MÖLNLYCKE HEALTH CARE AB, Göteburg (SE)

( * ) Notice: Subject to any disclaimer, the term of this patent is extended or adjusted under 35 U.S.C. 154(b) by 0 days.

This patent is subject to a terminal disclaimer.

(21) Appl. No.: 14/131,022

(22) PCT Filed: Jul. 23, 2012

(86) PCT No.: PCT/EP2012/003086
§ 371 (c)(1),
(2), (4) Date: Mar. 4, 2014

(87) PCT Pub. No.: WO2013/013799
PCT Pub. Date: Jan. 31, 2013

(65) Prior Publication Data
US 2014/0221944 A1 Aug. 7, 2014

(30) Foreign Application Priority Data
Jul. 23, 2011 (EP) .................................. 11006057

(51) Int. Cl.
| A61L 26/00 | (2006.01) |
| A61M 1/34 | (2006.01) |
| A61K 38/42 | (2006.01) |
| A61M 35/00 | (2006.01) |
| C07K 14/805 | (2006.01) |

(52) U.S. Cl.
CPC .......... *A61L 26/0047* (2013.01); *A61K 38/42* (2013.01); *A61L 26/0066* (2013.01); *A61L 26/0076* (2013.01); *A61M 1/34* (2013.01); *A61M 1/3403* (2014.02); *A61M 35/003* (2013.01); *C07K 14/805* (2013.01); *A61L 2300/252* (2013.01); *A61L 2300/412* (2013.01); *A61M 2202/0433* (2013.01); *F04C 2270/041* (2013.01)

(58) Field of Classification Search
None
See application file for complete search history.

(56) References Cited

U.S. PATENT DOCUMENTS

| 2,527,210 | A | | 10/1950 | Bower |
| 4,776,991 | A | * | 10/1988 | Farmer et al. ............ 264/4.3 |
| 5,476,764 | A | | 12/1995 | Bitensky |
| 5,985,332 | A | | 11/1999 | Barnikol et al. |
| 6,956,025 | B2 | | 10/2005 | Barnikol |
| 2003/0180365 | A1 | * | 9/2003 | Barnikol ............ A61K 8/22 424/487 |
| 2004/0023851 | A1 | | 2/2004 | Barnikol |
| 2004/0029780 | A1 | | 2/2004 | Barnikol et al. |
| 2005/0129747 | A1 | | 6/2005 | Barnikol et al. |
| 2008/0248012 | A1 | | 10/2008 | Suematsu |
| 2010/0278887 | A1 | | 11/2010 | Zal et al. |
| 2010/0311657 | A1 | * | 12/2010 | Abuchowski ........ A61K 9/0019 514/13.5 |

FOREIGN PATENT DOCUMENTS

| DE | 35 76 651 | | 11/1988 |
| DE | 37 14 351 | A1 | 11/1988 |
| DE | 38 41 105 | A1 | 6/1990 |
| DE | 44 18 937 | A1 | 8/1995 |
| DE | 100 31 742 | A1 | 1/2002 |
| DE | 100 31 744 | A1 | 1/2002 |
| DE | 100 31 740 | A1 | 2/2002 |
| EP | 0 854 151 | A1 | 7/1998 |
| EP | 0 857 733 | A2 | 8/1998 |
| EP | 1 723 968 | | 11/2006 |
| JP | 10-316579 | | 12/1998 |
| JP | 11-502821 | | 3/1999 |
| JP | 2011-98985 | | 5/2011 |
| WO | WO 1996/029346 | | 9/1996 |
| WO | WO 97/15313 | | 5/1997 |
| WO | WO 2001/034648 | | 5/2001 |
| WO | WO 2003/077941 | | 9/2003 |
| WO | WO 2003/094936 | | 11/2003 |
| WO | WO 2005/072773 | | 8/2005 |
| WO | WO 2008/034138 | A1 | 3/2008 |
| WO | WO 2010/144629 | | 12/2010 |

OTHER PUBLICATIONS

Arenberger et al. (Clinical results of the application of a hemoglobin spray to promote healing of chronic wounds, GMS, 2011 vol. 6(1)).*
Aerosols (http://aerosolsucp.blogspot.com/ , available online Mar. 31, 2008).*
Tiwari (Indian J Plast Surg. May-Aug. 2012;45(2) p. 364-373).*
International Search Report for International Application No. PCT/EP2012/003086, dated Nov. 30, 2012.
RCSB Protein Data Bank, Dec. 26, 2014, Human Carbonmonoxy Hemoglobin Bart's (GAMMA4), http://www.rcsb.org/pdb/explore/explore.do?structureId=113d.
Pai et al. Effect of Varying Oxygen Tensions on Healing of Open Wounds. Surgery Gynecology & Obstetrics (1972), 135:756-758.
Issues from Vth International Symposium on Blood Substitutes, San Diego, Calif., USA, Mar. 1993, Artificial Cells, Blood substitutes and Immobilization Biotechnology 22 (1994), vol. 2-vol. 4, Tables of Contents, 14 pages.
Bickar et al., "Carbon monoxide-driven reduction.." J. Biol. Chem. 194(259): 10777-10783.

(Continued)

*Primary Examiner* — James H Alstrum-Acevedo
*Assistant Examiner* — Tara L Martinez
(74) *Attorney, Agent, or Firm* — Kilpatrick Townsend & Stockton LLP

(57) ABSTRACT

The present invention refers to a composition, comprising hemoglobin or myoglobin, wherein in at least 40% of said hemoglobin or myoglobin the oxygen binding site is charged by a non-$O_2$ ligand, and at least one further ingredient, a method for preparing said composition and the use of hemoglobin or myoglobin charged with a non-oxygen ligand for external treatment of wounds.

15 Claims, 1 Drawing Sheet

(56) References Cited

OTHER PUBLICATIONS

Sawicki et al., "Quaternary conformational changes in human hemoglobin.." J. Biol. Chem. 1976(251): 1533-1542.
Plock, Jan A., et al. "Hemoglobin vesicles improve wound healing and tissue survival in critically ischemic skin in mice" Am. J. Physiol Heart Circ. Physiol (2009) 297: H905-H910.
Arenbergerova et al., "Effect of topical haemoglobin on healing in patients with venous leg ulcers," Der Hautarzt (2013), pp. 1-7.
Bateman, Sharon Dawn., "Topical haemoglobin spray for diabetic foot ulceration," British Journal of Nursing (Tissue Viability Supplement) (2015), vol. 24, No. 12, pp. S20-S25.
Hunt, Sharon Dawn, "Topical oxygen-haemoglobin use on sloughy wounds: positive patient outcomes and the promotion of self-care," Wounds UK (2015), vol. 11, No. 4, pp. 90-95.
Petri et al., "Photoacoustic imaging of real-time oxygen changes in chronic leg ulcers after topical application of a haemoglobin spray: a pilot study," Journal of Wound Care (2016), vol. 25, No. 2, pp. 1-5.
Amberson, W.R., et al., "Clinical experience with hemoglobin-saline solutions," J Appl Physiol (1949) 1(7): p. 469-89.
Collier, C.R., "Oxygen affinity of human blood in presence of carbon monoxide," J Appl Physiol (1976) 40(3): p. 487-90.
Guzman, J.A., "Carbon monoxide poisoning," Crit Care Clin (2012) 28(4): p. 537-48.
Henkel-Hanke, T., et al., "Artificial oxygen carriers: a current review," AANA Journal (2007) 75(3): p. 205-11.
Jahr, J.S., et al., "Hemoglobin-Based Oxygen Carriers: History, Limits, Brief Summary of the State of the Art, Including Clinical Trials," Chemistry and Biochemistry of Oxygen Therapeutics (2011) p. 301-316.

Müller et al. Die Hyperbare Oxygenation (HBO) bei Wundheilungsstörungen. Hartmann Wund [Wound] Forum 1 (1999),17-25.
Omaye, S.T., "Metabolic modulation of carbon monoxide toxicity," Toxicology (2002) 180(2): p. 139-50.
Page, T.C., et al., "Oxygen transport by erythrocyte/hemoglobin solution mixtures in an in vitro capillary as a model of hemoglobin-based oxygen carrier performance," Microvasc Res (1998) 55(1): p. 54-64.
Russell, M.A., "Blood carboxyhaemoglobin changes during tobacco smoking," Postgrad Med J (1973) 49(576): p. 684-7.
Sakai, H., et al., Purification of concentrated hemoglobin using organic solvent and heat treatment. Protein Expr Purif (1993) 4(6): p. 563-9.
Scholander, P.F., "Oxygen transport through hemoglobin solutions," Science (1960) 131(3400): p. 585-90.
Sellards, A.W., et al., The Preparation of Hemoglobin for Clinical Investigations. J Med Res (1917) 37(1): p. 161-70.
Silverman, T.A., et al., "Hemoglobin-based oxygen carriers: current status and future directions," Transfusion (2009) 49(11): p. 2495-515.
Silverstein, P., "Smoking and wound healing," Am J Med (1992) 93(1a): p. 22s-24s.
Sloan, A., et al., "The effects of smoking on fracture healing," Surgeon (2010) 8(2): p. 111-6.
Weiskopf, R.B., Introduction, Chemistry and Biochemistry of Oxygen Therapeutics (2011) p. 1-7.
Wu, L., et al., "Carbon monoxide: endogenous production, physiological functions, and pharmacological applications," Pharmacol Rev (2005) 57(4): p. 585-630.
Japanese Notice of Reasons for Rejection dated Feb. 2, 2016 for Japanese Application No. 2014-521979 which corresponds in priority to the above-identified subject U.S. application.

* cited by examiner

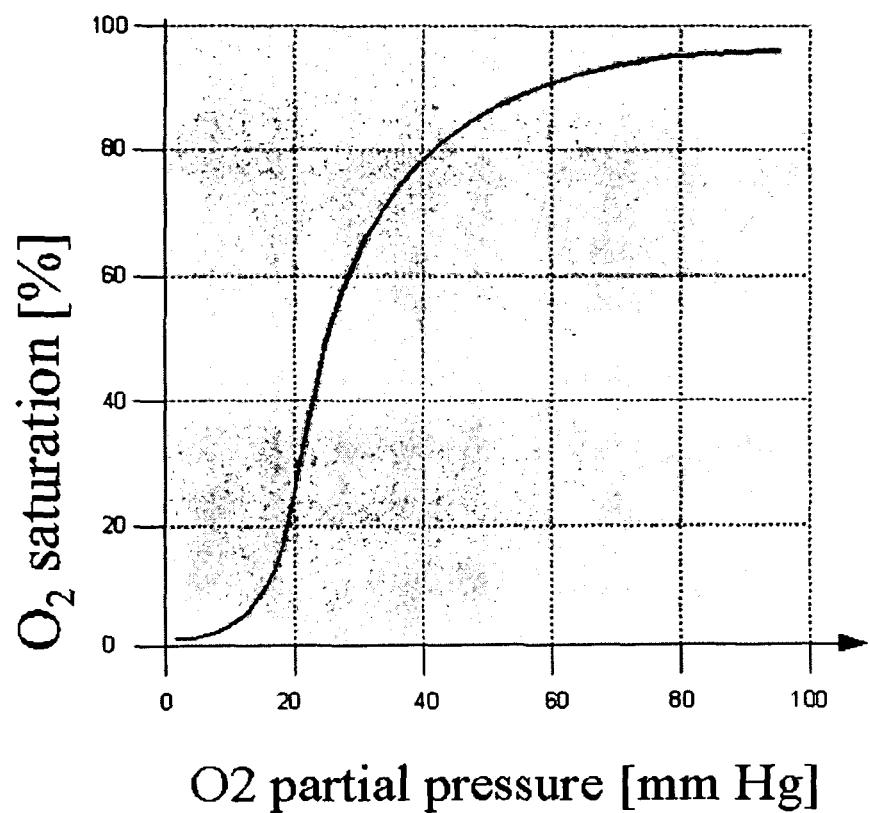

WOUND SPRAY

CROSS-REFERENCE TO RELATED APPLICATIONS

This application is the U.S. National Phase under 35 U.S.C. § 371 of International Application PCT/EP2012/003086, filed Jul. 23, 2012, which claims priority to EP 11006057.1, filed Jul. 23, 2011.

The present invention refers to a composition, comprising hemoglobin or myoglobin, wherein in at least 40% of said hemoglobin or myoglobin the oxygen binding site is charged by a non-$O_2$ ligand, and at least one further ingredient, a method for preparing said composition and the use of hemoglobin or myoglobin charged with a non-oxygen ligand for external treatment of wounds.

Different methods are used for treating wounds, depending on their status. First, a wound that is still open preferably should be disinfected and thereby protected against negative external influences. This can be done by means of suitable disinfectant solutions or spray-on bandages or also by applying iodine solution. Actual wound healing must then take place from inside. This means that the blood vessels still in place must supply the destroyed tissue with sufficient amounts of substrates, so that the tissue repair mechanism can start.

Wounds can be caused by various factors, like e.g. injuries or also after operations or traumatic events.

On the other hand, it is known that wound formation, particularly also chronic wounds, can also be provoked by diseases, in which degeneration and/or constriction of large and/or small blood vessels occurs. This may be the result e.g. in the case of older patients, of extended stays in bed (decubitus) or of diabetes mellitus which may lead to degeneration and arteriosclerosis (P. Carpenter, A. Franco, Atlas der Kapillaroskopie [Atlas of Capillaroscopy], 1983, Abbott, Max-Planck-Inst. 2, D-Wiesbaden) of the large and small blood vessels (macroangiopathy and microangiopathy of the arteries). It was also shown that an oxygen deficiency (hypoxia) is present in the wound area. 40 mmHg is considered to be a critical value (C. D. Müller et al., Hartmann Wund [Wound] Forum 1 (1999), 17-25).

The blood flows to the tissues, including the skin, through the arteries and supplies the cells with substrates required for life. Any degeneration of the blood vessels results in a deficient supply of substrates to the cells, leading to their death. The substrates must pass the last, seemingly insignificant gap of approximately 20 μm from the smallest blood vessels (capillaries) to the cells by diffusion; in this connection, oxygen plays a special role, because it is difficult for the organism to handle this substrate.

There are three main problems involved:
(1) It is true that oxygen is absolutely essential for life (a human being is brain-dead after only approximately five minutes if his/her brain does not receive oxygen), but at the same time, oxygen is highly toxic (a newborn that receives respiration treatment with pure oxygen will die-after only a few days).
(2) Oxygen has very little solubility in an aqueous medium. This results, according to FICK's first law, in a lower diffusion rate of oxygen. In addition, there is a fundamental law of diffusion, namely SMOLUCHOWSKI's and EINSTEIN's law, that states that the diffusion speed (of oxygen) decreases with an increasing diffusion distance. Now the diffusion constant of oxygen is so low that the diffusion speed at a diffusion distance of as little as 20 μm is only 5% of the initial value. A water layer of e.g. 50 μm represents a nearly complete oxygen insulation for the cells. Oxygen is transported along the long paths in the organism from the lungs to the tips of the toes with the bloodstream, bound to hemoglobin, and only in this way is able to overcome the long distances in a manner that is suitable for the organism.
(3) For oxygen, in contrast to glucose, for example, there is no storage area in the body, therefore this substrate must be available to the cells at all times and quickly, in a sufficient amount; oxygen is a so-called immediate substrate necessary for life.

An intact organism has solved these problems by using several mechanisms. The toxic effects of oxygen are avoided in that the latter binds during transport to hemoglobin and thereby remains harmless. At the same time, the free oxygen is diluted and thereby further loses its harmful oxidative potential. Nevertheless, it is instantaneously available in a sufficient amount, because the binding to hemoglobin is reversible. The problem of the low diffusive range is solved in that the organism has developed a very finely branched blood vessel network (capillary network), which ensures that on the average, every cell is at a distance of at most 25 μm from a capillary; in this way, the diffusion path of oxygen in the organism remains below the critical length of 50 μm. In addition, a cell can be diffusively supplied with oxygen from several sides; this represents a safety mechanism. The immediate availability, in accordance with the demand (oxygen is not allowed to be available in excess, otherwise it would have a harmful effect) is achieved, in the organism, by means of vascular regulation of the blood vessel flow, which controls perfusion and thereby optimizes the supply of oxygen.

If there is an open wound surface, the oxygen supply to the cells is interrupted. The oxygen supply from air outside is poor because an aqueous liquid film is laying on the (tissue) cell layer, which film, as explained, forms a diffusive oxygen barrier. Fresh wounds in normal tissue can heal in a few days, if the oxygen supply from underneath, in other words from the inside, is sufficient. However, it was shown in animal experiments that even fresh wounds heal better if the oxygen concentration of the surrounding air is increased (M. P. Pai et al., Sug. Gyn. Obstet. 135 (1972), 756-758). Older, particularly chronic wounds are known to heal very slowly, if at all, due to their oxygen deficiency.

To heal chronic wounds better, as well, so-called hyperbaric oxygen therapy (HBO) has been used. In this treatment, patients are placed in pressurized chambers, where they are subjected to an excess pressure of pure oxygen of about 3 bar for a certain period of time (C. D. Müller et al., Hartmann Wund Forum 1 (1999), 17-25). In fact, wound healing may be increased by this method. However, the effect decreases with the number of treatments.

U.S. Pat. No. 2,527,210 describes a hemoglobin solution that can allegedly be used for the treatment of wounds, both intravenously and topically, for example by spraying. In this description, the hemoglobin is obtained from fresh erythrocytes that are subjected to freezing shock after centrifugation and drawing off the blood plasma fraction. This results in cell lysis, and hemoglobin is released. The broken cell walls are also present in the product. This formulation is a concentrated cell detritus (cell fragments). In this way, an antiseptic cover effect such as otherwise achieved with iodine solution, after having added 5% sodium sulfide, is supposed. In other words, the wound is merely closed. Oxygen transport is not mentioned there.

WO 97/15313 describes the therapeutic use of hemoglobin for improving wound healing. For this purpose, hemoglobin free of stroma and pyrogens is intravenously administered to the patients, particularly after operations and traumatic events to increase the blood pressure. In particular, a hemoglobin cross-linked with diaspirin is used for this purpose.

WO 2003/077941 teaches the treatment of open wounds with a hemoglobin solution comprising isolated and optionally crosslinked hemoglobin. The solutions were freshly prepared with hemoglobin from pig blood and applied to chronic wounds.

During the preparation and storage of oxygen carriers on basis of hemoglobin or myoglobin they can lose their functionality partially or completely. To prevent this it is desirable to stabilize the oxygen carriers that they remain usable and able to transport oxygen.

Generally, there are different approaches to the preparation of artificial oxygen carriers; one of them is the preparation of suitable solutions of native or chemically modified hemoglobins (see "Issues from Vth International Symposium on Blood Substitutes, San Diego, Calif., USA, March 1993", Artificial Cells, Blood Substitutes, and Immobilization Biotechnology 22 (1994), vol. 2-vol. 4). One problem in the handling of such pharmaceutical preparations as artificial oxygen carriers is their increasing inactivation by spontaneous oxidation to methemoglobin which is no longer able to transport oxygen. This occurs usually during preparation by the producer and the subsequent storage.

Several approaches for solving this problem are described. Either it is tried to minimize the degree of oxidation of hemoglobin, or to reduce the oxidized hemoglobin back again.

One possibility for prevention of spontaneous oxidation is deoxygenating the hemoglobin (i.e., entirely removing oxygen from the preparation), since desoxyhemoglobin oxidizes much more slowly to methemoglobin than oxyhemoglobin.

Further it is possible to minimize the amount of oxidation by storage and/or preparation at the lowest possible temperature (for aqueous solutions, at about 4° C.).

Additionally, the rate of oxidation of hemoglobin depends on the hydrogen ion concentration, i.e., the pH. For example, for native human hemoglobin there is a minimum in the interval between pH 7.5 and 9.5.

Also, the addition of certain alcohols can diminish the oxidation of hemoglobin. Some of them work even in low concentration. One problem is the toxicity of these alcohols.

Certain metal ions ($Cu_2^+$, $Fe_3^+$ etc.) catalyze the spontaneous oxidation of hemoglobin. They can be rendered ineffective by complexing with EDTA (ethylenediaminetetraacetic acid), although EDTA itself promotes the spontaneous oxidation of hemoglobin.

Protection of artificial oxygen carriers against oxidation may further be achieved by the addition of reducing substances. Under certain circumstances they even result in a reactivation of oxidized hemoglobin.

EP 0 857 733 describes that hemoglobin may be stabilized by binding a ligand, in particular carbon monoxide, to the oxygen binding site. It was found that such a carbonylhemoglobin can be applied to an organism without de-ligandation and is suitable as an oxygen carrier inside of the blood stream.

The object of the present invention is to provide a product for the external treatment of wounds, which increases the wound healing, is easy in handling and storable.

This object is met, according to the invention, by a composition, comprising (a) An oxygen carrier, preferably hemoglobin or myoglobin, wherein in at least 40% of said oxygen carrier the oxygen binding site is charged by a non-$O_2$ ligand, and
(b) at least one further ingredient, selected from electrolyte(s) preservative(s), stabilizer(s), anti-flocculant(s), anticoagulant(s), pH buffering agent(s), solvent(s), antioxidant(s), film-forming agent(s) and crosslinking agent(s)

and the use of an oxygen carrier, preferably hemoglobin or myoglobin charged on its oxygen-binding site with a non-$O_2$ ligand for the preparation of an agent or composition for the external treatment of wounds.

According to the invention preferably a natural (native) oxygen carrier, particularly hemoglobin or myoglobin or a modified derivative thereof, or mixtures thereof, is/are used. Hemoglobin or myoglobin of human or animal origin, in particular of equine, bovine or preferably porcine origin, is particularly suitable for the present invention. Human or porcine hemoglobin, which is natural or modified as described below, is particularly preferred as an oxygen carrier. The oxygen carrier may be freshly isolated from human or animal blood or may be artificially prepared.

Mixtures of natural and modified oxygen carrier can also be used, such as, for example, in a ratio of 20:1 to 1:20, with reference to weight. Further, mixtures of hemoglobin and myoglobin, or their modified derivatives may be used in the aforementioned ratio of 20:1 to 1:20.

In a further embodiment the oxygen carrier may be modified. The modification can be an intramolecular cross-linking, polymerization (intermolecular cross-linking), pegylation (covalent linking with polyalkylene oxides), modification with chemically reactive effectors such as pyridoxal-5'-phosphate or 2-nor-2-formyl-pyridoxal-5'-phosphate, or also with chemically non-reactive effectors of the oxygen bond, such as 2,3-bisphosphoglycerate, inositol hexaphosphate, inositol hexasulfate, or mellitic acid, or a combination thereof. Such modifications are known and described, for example, in DE-A 100 31 744, DE-A 100 31 742, and DE-A 100 31 740. Cross-linking of oxygen carriers is also described in DE 197 01 37, EP 97 1000790, DE 44 18 937, DE 38 41 105, DE 37 14 351, DE 35 76 651.

Examples for modified oxygen carriers are hemoglobins having a molecular weight of 65,000 to 15,000,000, such as intramolecularly cross-linked molecules according to WO 97/15313, particularly polymer products as well as intermolecularly cross-linked products having an average molecular weight of 80,000 to 10,000,000 g/mol, particularly 100,000 to 5,000,000, or analogously produced myoglobins having a molecular weight of 16,000 to 5,000,000, particularly 100,000 to 3,000,000, preferably 1,000,000 g/mol. Those oxygen carriers that are polymerized, for example using cross-linking agents known for intermolecular modification, such as bifunctional cross-linking agents like butadiene diepoxy, divinyl sulfone, diisocyanate, particularly hexamethylene diisocyanate, cyclohexyl diisocyanate, and 2,5-bisisocyanatobenzol sulfonic acid, di-N-hydroxy succinimidyl ester, diimidoester, or dialdehyde, particularly glyoxal, glycol aldehyde that reacts analogously, or glutardialdehyde may be used.

Furthermore, products which are polymerized in this manner and pegylated with a polyethylene glycol or suitable derivatives thereof may be used. This includes, for example, polyethylene oxide, polypropylene oxide, or a copolymer of ethylene oxide and propylene oxide, or an ester, ether, or ester amide thereof. It may be suitable if the covalently linked polyalkylene oxide has a molar mass of 200 to 5000 g/mol.

For covalent linking of the polyalkylene oxides, those derivatives of polyalkylene oxide that contain a linking agent already covalently bound with a functional group, thereby allowing a direct chemical reaction with amino, alcohol, or sulfhydryl groups of the hemoglobins, forming covalent links of the polyalkylene oxides may be suitable, for example polyalkylene oxides with reactive N-hydroxy succinimidyl ester, epoxy (glycidyl ether), Idehyde, isocyanate, vinyl sulfone, iodacetamide, imidazolyl formate, tresylate groups, and others. Many such monofunctionally activated polyethylene glycols are commercially available.

If modified oxygen carriers are used, modified cross-linked (intramolecular or intermolecular), or cross-linked and pegylated hemoglobin products having an average molecular weight of 250,000 to 750,000 g/mol, or myoglobin products having an average molecular weight of 50,000 to 750,000 g/mol, are preferred.

According to the particular preferred embodiment freshly isolated hemoglobin or myoglobin of human or animal origin, in particular of porcine origin is used for preparation of the inventive composition.

According to the present invention at least 40% of the oxygen binding sites of the oxygen carrier are charged with a non-$O_2$ ligand. Preferably at least 50%, preferably at least 60%, more preferred at least 70%, even more preferred at least 80%, particularly preferred at least 90% or 95% of the hemoglobin or myoglobin is provided in ligand-charged form. This charge may already be applied during isolation of the carrier or after its further purification, however, it is particularly preferred to carry out the isolation of the oxygen carrier in its protected form, which means that during isolation or purification the ligand is provided to/contacted with the oxygen carrier.

The non-$O_2$ ligand preferably is carbon monoxide (CO) or nitrogen monoxide (NO) or a mixture thereof. Both ligands have a high affinity for the hemoglobin/myoglobin $O_2$ binding site(s) and serve as a protector against oxidation of the central $Fe^{3+}$ Ion of the heme.

The charged oxygen carrier(s) is/are preferably dissolved in an aqueous or organic medium, wherein an aqueous solution is preferred, in an amount of 0.1 to 35 wt.-%, preferably 0.1 to 20 wt.-%, more preferred 0.1 to 15 wt.-%, to be ready for application.

The composition according to the present invention further comprises at least one further additive, preferably selected from the group comprising electrolyte(s), stabilizer(s), anti-flocculant(s), preservative(s), pH buffering agent(s), solvent(s), antioxidant(s) and film-forming agent(s), more preferred selected from electrolyte(s), stabilizer(s), anti-flocculant(s), preservative(s) and pH buffering agent(s). Most preferred the composition is in form of a solution and comprises at least an electrolyte and optionally a stabilizer.

The solution may comprise physiologically compatible electrolytes, such as salts, in suitable or desired amounts. The electrolytes may be present in amounts of 0.1 to 30 wt.-%, preferably 0.1 to 10%, but preferably are present in a physiological concentration, respectively. Preferably the composition comprises a salt in the before mentioned amounts, like e.g. NaCl, KCl, $NH_4Cl$, $CaCO_3$, $Na_2CO_3$, $K_2CO_3$, $MgSO_4$, $Na_2SO_4$, $CaCl_2$, $MgCl_2$, sodium citrate, sodium lactate or mixtures of the mentioned or similar without being restricted to these examples. The most preferred salt is NaCl, particularly in a concentration of 0.9% (isotonic solution).

According to the invention it is particularly preferred that the composition comprises a compound acting as a stabilizer and/or anti-flocculant for proteins in particular for the hemoglobin/myoglobin, such as N-acetyl cysteine, cysteine, N-actyl methionine, methionine, non-chaotropic salts, polyols, like sugars, preferably disaccharides, and amino acids preferably each in amounts of 0.001 wt.-% to 20 wt.-%.

The polyols which may be employed are preferably low molecular weight polyols although polymeric derivatives may be employed. Such polyols include ethylene glycol, glycerol, erythritol and mannitol. Cyclic polyols which may be employed incorporate one or more alicyclic rings and may have at least one side chain. Preferred polyols include disaccharides and sugar alcohols, for example lactitol, sorbitol and inositol. Compounds having 2 to 10 hydroxyl groups are preferred. The amount of the polyol may be in the preferred range 0.001 to 20% more preferably 1 to 15% most preferably 2 to 10% w/v.

Further the protein stabilizer additive may be selected from a tris(hydroxymethyl)methyl compound of formula 1;

$$(HOCH_2)_3C-R \qquad (1)$$

wherein R is: $C_1$-$C_4$ alkyl, substituted $C_1$-$C_4$ alkyl, $NH_2$, $NHC(CH_2OH)_3$, $C_1$-$C_4$ hydroxyalkyl; $C_1$-$C_4$ alkyl carboxylate, $NR^1R^2$ (wherein $R^1$ and $R^2$ may be independently: H, $C_1$-$C_4$ alkyl, $C_1$-$C_4$ alkyl sulphonate, $C_1$-$C_4$ hydroxyalkyl sulphonate). Examples of preferred compounds of formula (1) include: tris(hydroxymethyl)ethane; 1,1',1''-tris(hydroxymethyl)propane; tris(hydroxymethyl)aminomethane or salts thereof for example chloride, maleate, phosphate, succinate salts; 1,3 bis[tris(hydroxymethyl)methylamino] propane; bis(2hydroxyethyl)amino-tris(hydroxymethyl) methane; N [tris(hydroxymethyl)methyl]-2-aminoethane sulphonate; N [tris(hydroxymethyl)methyl]-3-aminopropane sulphonate; N [tris(hydroxymethyl)methyl]-3-amino-2-hydroxypropane sulphonate; N-[tris(hydroxymethyl) methyl]-glycine. Said compounds as well may be added in the preferred range of 0.001 to 20% more preferably 1 to 15% most preferably 2 to 10% w/v.

Further the protein stabilizer additive may be selected from a polyelectrolyte. The polyelectrolyte may be a cationic or anionic polyelectrolyte. Amphoteric polyelectrolytes may also be employed. The cationic polyelectrolyte is preferably a polymer with cationic groups distributed along the molecular chain.

The cationic groups, which are preferably quaternary ammonium derived functions, may be disposed in side groups pendant from the chain or may be incorporated in it. Examples of cationic polyelectrolytes include: Copolymers of vinyl pyrollidone and quaternary methyl methacrylate eg Gafquat series (755N, 734, HS-100) obtained from ISP; substituted polyacrylamides; polyethyleneimine, polypropyleneimine and substituted derivatives; polyamine homopolymers (Golchem CL118); polyamine co-polymers (eg condensates of epichlorohydrin and mono or dimethylamine); polydiallyl dimethyl ammonium chloride (polyDADMAC); substituted dextrans; modified guar gum (substituted with hydroxypropyltrimonium chloride); substituted proteins (eg quaternary groups substituted on soya protein and hydrolysed collagen); polyamino acids (eg polylysine); low molecular weight polyamino compounds (eg spermine and spermidine). Natural or artificial polymers may be employed.

Cationic polyelectrolytes with MW 150 to 5,000,000, preferably 5000 to 500,000, more preferably 5000 to 100, 000 may be employed. An amount of 0.01 to 10% is preferred, more preferably 0.1 to 2%, especially 0.05 to 5% w/v.

The anionic polyelectrolyte is preferably a polymer with anionic groups distributed along the molecular chain. The anionic groups, which may include carboxylate, sulphonate, sulphate or other negatively charged ionisable groupings, may be disposed upon groups pendant from the chain or bonded directly to the polymer backbone. Natural or artificial polymers may be employed.

Examples of anionic polyelectrolytes include: Gantrez (Sseries, AN-series); alginic acid and salts; carboxymethyl celluloses and salts; substituted polyacrylamides (e.g. substituted with carboxylic acid groups); polyacrylic acids and salts; polystyrene sulphonic acids and salts; dextran sulphates; substituted saccharides eg sucrose octosulphate; heparin. Anionic polyelectrolytes with MW of 150 to 5,000,000 may be used, preferably 5000 to 500,000, more preferably 5000 to 100,000. An amount of 0.01% to 10% is preferred especially 0.05 to 5% more especially 0.1 to 2% w/v.

A particular preferred stabilizer is N-acetyl cysteine in an amount of 0 to 10%, preferably 0.01 to 5%.

Further the composition may contain any preservative like e.g. phenoxyethanol, isothiazoline, sorbic acid or any other suitable preservative known to skilled persons.

The composition may further preferably comprise any buffering agent. All of the commonly known buffering agents may be used, like Tris/HCl, $K_2HPO_4/KH_2PO_4$, $Na_2HPO_4/NaH_2PO_4$, MOPS (3-(N-morpholino)propanesulfonic acid), HEPES (4-2-hydroxyethyl-1-piperazineethanesulfonic acid), TAPS (3-{[tris(hydroxymethyl)methyl]amino}propanesulfonic acid), Bicine (N,N-bis(2-hydroxyethyl)glycine), Tricine (N-tris(hydroxymethyl)methylglycine), TES (2-{[tris(hydroxymethyl)methyl]amino}ethanesulfonic acid), PIPES (piperazine-N,N'-bis(2-ethanesulfonic acid)), SSC (saline sodium citrate), MES (2-(N-morpholino)ethanesulfonic acid) without being limited to these.

Suitable solvents in the composition according to the invention are preferably water or aqueous solutions, organic solvents like alcohol, preferably ethanol, or polyethyleneglycol (PEG). Mixtures of said solvents as well can be used. Further natural oils may be used as a solvent for some of the ingredients and the composition may be provided as an emulsion. A particularly preferred solvent is water or an aqueous solution.

Antioxidants useful for the present composition may be e.g. vitamin C, vitamin E, flavonoids, carotinoids, or salts or derivatives thereof.

Preferred film-forming agents are such agents commonly used in cosmetic application, like e.g. Acrylamide/Sodium, Acrylate Copolymer, Acrylates/Acrylamide Copolymer, Butyl Ester of PVM/MA Copolymer, Carboxymethyl Chitin, Chitosan, Hydroxypropyl Cellulose, Polyquaternium-36, PVP, PVP/VA Copolymer, VA/Crotonates Copolymer or Vinyl Caprolactam/PCP/Dimethylaminoctyl Methylacrylate Copolymer.

All the above mentioned additives may be present in an amount of 0 to 20, preferably 0.001, 0.01, 0.05 or 0.1 to 10, more preferably 0.5 to 5% (w/v), if not otherwise stated above.

If desired, further additives may be present, in particular in an amount of 0 to 20, preferably 0.1 to 20, preferably 0.2 to 15, particularly 0.5 to 10 wt.-%. Preferred additives are nutrients for cells. They can be selected from glucose, e.g. in amounts of 0.1 to 5 wt.-%, insulin in amounts of up to 25 IU/ml, the natural amino acids, in particular cysteine, e.g. 0.1 to 5 wt.-%, or tissue factors, such as interleukins in physiological amounts, up to a 10-fold amount thereof.

Preferably the composition represents an aqueous solution comprising
(a) an oxygen carrier, preferably hemoglobin or myoglobin, wherein in at least 40% of said oxygen carrier the oxygen binding site is charged by a non-$O_2$ ligand, and
(b) at least one further ingredient, selected from electrolyte(s) preservative(s), stabilizer(s), anti-flocculant(s), anticoagulant(s), pH buffering agent(s), antioxidant(s), organic solvent, film-forming agent(s) and crosslinking agent(s).

In a preferred embodiment of the present invention the composition comprises an oxygen carrier, which is isolated from whole blood of a human or animal, preferably from pigs.

Accordingly it is a further aspect of the invention to provide a process for the purification of an oxygen carrier usable for the composition of the present invention from whole blood.

For preparation of the composition in the preferred embodiment the oxygen carrier is isolated from blood of a human or animal and is further purified to be essentially free of plasma and cellular membrane constituents.

With "essentially free" is meant that the considered compound or composition doesn't comprise more than 20%, preferably not more than 10%, even more preferred not more than 5% and particularly preferred not more than 2% or less than 1% of the mentioned undesired compound(s).

The purification can comprise any suitable means or method steps, like e.g. selective lysis or precipitation, centrifugation, ultracentrifugation, fractionated centrifugation, chromatography methods like anion exchange chromatography, size exclusion chromatography, affinity or adsorption chromatography, gel filtration or molecular sieve chromatography, or dialysis, without being restricted to these examples, as far as by the applied methods the oxygen carrier is denaturated as less as possible. Preferably during isolation and purification the oxygen carrier remains essentially in solution.

When the oxygen carrier is isolated from whole blood, it is preferred that either the cells comprising the oxygen carrier are separated from other blood components or said cells are selectively lysed to deliver the (soluble) oxygen carrier into solution and thereafter the non-soluble components are separated. A combination of the two methods as well is suitable. The lysis of the oxygen carrier containing cells may be carried out by any suitable lysis method, e.g. chemical lysis, osmotical lysis, mechanical lysis, thermal lysis or similar.

Cell debris may be separated by any suitable means or method. This includes e.g. centrifugation, filtration, sedimentation and decantation, dialysis or any similar method.

For separating non-lysed cells or the cell debris from the solved oxygen carrier a common method is pelletation of the solid material. For example a centrifugation step may be carried out. Centrifugation with 2 to 5000×g usually is sufficient for pelleting cells and cell debris.

For pelleting further non-solved components, e.g. any precipitate developed during the purification process, at any time during the purification process further centrifugation steps may be carried out, in particular centrifugation steps using higher forces, up to ultracentrifugation with up to $10^6 \times g$.

The purification of the oxygen carrier containing solution additionally or as an alternative to any centrifugation step may comprise at least one filtration step, preferably at least two, three or more filtration steps. This can be carried out either by using at least one, preferably at least two, more preferably at least three filters (if more than one filter is used in the present application we use the term "filter cascade"), or by one, two, three or more separate filtration steps.

Said filter cascade or the different filtering steps may include two, three, four, five ore more filters of different type, different material and or different pore sizes. Further a deep bed filter like e.g. glass wool or similar may be used, preferably as a first filter material to retain coarse cell debris. If more than one filter is used, it is preferred to use filters providing different pore diameters in decreased order. For example, if three different filters are used, the first filter (after the deep bed filter) may have an average pore size of 1 to 0.5 µm, the second filter may have a pore size of 0.7 to 0.3 µm and the third a pore size of 0.4 to 0.1 µm, wherein independent from the overlapping ranges cited before the following filter in any case has a smaller pore size than the filter prior to that. By said filtering step(s) solid and precipitated material having a larger size than the pore size of the used filters is essentially removed.

Further an ultrafiltration step may be included in the purification process for purifying the oxygen carrier(s). By such an ultrafiltration step non-desired solved macromolecules can be separated. Preferably the size exclusion limit is selected to separate macromolecules which are bigger (larger, higher molecular weight) than the desired oxygen carriers, accordingly said macromolecules are retained by the filter. Due to the molecular weight of hemoglobin of about 64,000 Dalton the size exclusion limit of the ultrafiltration filter should be higher. To make sure that the yield of hemoglobin is not decreased by the ultrafiltration step, it is preferred to select the size exclusion of the filter at about 100,000 Dalton, preferably at about 200,000 Dalton, more preferred at about 300,000 Dalton without being restricted to these values.

Additionally or as an alternative any suitable chromatography step can be carried out. A particularly preferred type of chromatography is ion exchange or size exclusion chromatography.

The same result may be obtained by a dialysis step using a dialysis membrane providing the above mentioned size exclusion limits, allowing the oxygen carrier to pass, but retaining the macromolecules having a higher molecular size.

To lower the amount of small molecular weight compounds in solution an additional dialysis step may be carried out using a dialysis membrane having a size exclusion limit of about 50.000 Dalton, allowing smaller molecules to pass, but retaining the oxygen carrier.

To diminish the virus and/or microorganism contamination in the composition it is particularly preferred to include a step of virus content degradation in the purification process. The virus content is reduced by this step, preferably to a burden of less than 10, preferably less than 5, more preferably less than 2 virus particles per ml, and even more preferred to 0. In this step it is preferred that the solution comprising the oxygen carrier is passed through a virus content degradation filter ("virus filter"). Such filters are commonly known and available on the market. Examples are Sartorius Virosart® CPV, Planova® 15N, 20N, Millipore Viresolve® NFP or PALL Pegasus® Grade LV6, without being limited to these. Alternatively or additionally, preferably after the passage through the filter, a treatment with UV light, in particular UV light of a wavelength of 245 nm may be applied to dispatch any remaining viruses.

Optionally at any stage during the process of isolation of the oxygen carrier at least one heating step may be carried out. This step comprises the heating of the oxygen carrier containing suspension or solution during the isolation procedure to a temperature in the range of 40 to 85° C., preferably 60 to 80° C., more preferred in the range of 65 to 75° C. The heating step is carried out preferably for 10 min to 6 hours, preferably for 20 min to 4 hours and most preferred for 30 min to 3 hours and may comprise several different temperatures within the before mentioned range.

According to the process of the present invention it is preferred that the oxygen carrier remains in solution during the whole purification process. Further it is preferred that the oxygen carrier remains in solution during the whole purification process and during preparation of the composition of the present invention. This means that it is preferred that the oxygen carrier is not precipitated in the process of the present invention and accordingly remains in its natural three-dimensional structure as present in its natural environment.

In a particular preferred process according to the present invention the process for purifying an oxygen carrier from whole blood comprises at least the steps:
(a) separating plasma of the whole blood
(b) lysing the red blood cells
(c) charging the oxygen carriers with the ligand
(d) heating the sample to a temperature in the range of 40 to 85° C.
(e) separating the oxygen carrier from any non-desired blood components.

By these steps an oxygen carrier containing solution is obtainable which can be used for the preparation of the composition of the present invention. In particular the oxygen carrier containing solution obtainable by these steps may be concentrated to a desired amount of the oxygen carrier and to this solution the at least one further ingredient(s) is/are added to obtain the composition of the present invention.

Step (a) of the present method can be carried out by any of the commonly used methods for separating plasma from whole blood, preferably by centrifugation or filtration. By centrifugation for about 30 min at about 2000 to 5000 rpm, e.g. 4000 rpm red blood cells are pelleted, whereas soluble compounds and white blood cells remain predominantly in the supernatant. By repeating resuspension and pelleting of the red blood cells e.g. 2 to 5 times, separation of the red blood cells from the undesired blood compounds can be increased.

Step (b) is preferably carried out by adding water, preferably distilled water or a suitable sub-isotonic buffer, preferably a phosphate buffer, to the thickened blood of step (a). After lysing the red blood cells with water or a sub-isotonic buffer preferably a salt is added to the solution/suspension to obtain physiological concentration of said salt in solution. Preferably NaCl is added to an amount of 0.9% in solution.

Step (c) may be carried out after step (a), after step (b), after step (d) or after step (e), but is preferably carried out at least after step (b). It is particularly pointed out that step (c) is not necessarily carried out immediately as a next step after step (b), but as well can be carried out or repeated after step (d), after step (e) or any following treatment steps. The charging of the oxygen carrier in the solution/suspension may be carried out by introducing gas in the solution/suspension, preferably CO or NO gas or a mixture thereof. In a preferred embodiment CO gas is introduced into the solution/suspension for a time period long enough to obtain a >90% saturation in the solution/suspension, preferably a >95% saturation.

Step (d) may be carried out after step (a), after step (b), after step (c) or after step (e), but is preferably carried out after step (c). Further the heating can be repeated during the isolation procedure. This step comprises the heating of the oxygen carrier containing suspension or solution during the isolation procedure to a temperature in the range of 40 to 85° C., preferably 60 to 80° C., more preferred in the range of 65 to 75° C. The heating step is carried out preferably for 10 min to 6 hours, preferably for 20 min to 4 hours and most preferred for 30 min to 3 hours and may comprise several different temperatures within the before mentioned range.

In step (e) the oxygen carrier is purified from further non-desired ingredients still contained in solution, like non-lysed cells, cell debris, any precipitate or other non-soluble ingredients. Further the oxygen-carrier may be further purified by separating at least partially non-desired soluble compounds, like e.g. soluble macromolecules or soluble compounds having low molecular weight.

Accordingly said step (e) may include several single steps, like filtration, ultrafiltration, centrifugation, ultracentrifugation, chromatography, dialysis using different types of dialysis membranes providing different size exclusion limits, washing steps, concentration of the oxygen carrier content etc. Any of the methods cited above may be included in this purification step.

Preferably at least one centrifugation and/or at least one filtration step is comprised in step (e). E.g. the lysate may be spinned in a centrifuge to separate remaining cells and cell debris or it is filtered e.g. by a filter cascade as described above. The lysate can be as well first centrifuged and thereafter filtered, or it may be filtered in a first step through a deep bed filter and thereafter through at least one filter or a filter cascade. By the centrifugation or the deep bed filter the handling during any following filtering steps is simplified due to less material settling on and clogging the filter(s). If not a filter cascade is used, it is preferred that at least one filter is used allowing to retain essentially all of the solid materials contained in the suspension and allowing to pass all the solved components. In a more preferred embodiment at least one of the used filter(s) is able to retain as well microorganisms, acting as a sterile filter. Further preferred an ultrafiltration step and/or a step for diminishing the virus and/or microorganism content of the solution can be carried out. Accordingly it is preferred that after step (e) the oxygen carrier containing solution is essentially free of any non-solved particles, flocks or precipitate.

In step (e) additionally to any of the steps/methods cited above the solution comprising the desired oxygen carrier may be washed and/or concentrated. By "washing" is meant that molecules smaller than the desired oxygen carrier (having lower molecular weight) are separated, preferably by adding the same or a multifold (e.g. 5 to 10 fold) amount of an isotonic solution to the oxygen carrier containing solution and thereafter filtering the obtained (diluted) solution by a filter retaining the oxygen carrier and allowing smaller molecules to pass. For washing the solution preferably a 0.9% NaCl solution is used. The washing step may be repeated 2 or 3 or 4 or 5 or up to 10 times. A preferred embodiment is exemplified by the use of a filter having a size exclusion limit of 5,000 Dalton, 10,000 Dalton or 20,000 Dalton, allowing smaller molecules to pass. In this step the oxygen carrier containing solution (preferably after washing) may be concentrated to a desired concentration of the oxygen carrier, e.g. to a concentration of 50 g/l, 100 g/l or 200 g/l without being restricted to these amounts. Any desired concentration can be obtained either by concentrating by filtration or by adding 0.9% NaCl or a similar isotonic solution.

The so obtainable oxygen carrier containing solution can then be used to prepare the composition of the present invention by adding the at least one further ingredient described above to the solution in the desired amount.

In a preferred embodiment the composition of the present invention is prepared by adding to the oxygen carrier containing solution at least a preservative, preferably a pharmaceutically acceptable preservative like e.g. phenoxyethanol, parabenes, sodium benzoate, benzyl alcohol, hexachlorophen and an antioxidant and/or stabilizer like e.g. N-acetylcysteine, sodium octanoate, N-acetyl-I-tryptophanate, N-acetyl-methioninate, vitamin E, vitamin C, methyl prednisolone or mannitol. Additionally any of the further ingredients described above may be added additionally.

The finished composition may be sterilized again, if desired, e.g. by heating, filtration, centrifugation, addition of preservatives, vapour application, gas application or UV-application or a combination of at least two of them, preferably by a further sterile filtration step and is preferably filled in sterile containers or sterile bags for storing.

According to a preferred embodiment the sterile bags are positioned in an aerosol can for later use. One example can be a Bag-on-Valve system, comprising a bag, e.g. a laminated aluminium bag and an aluminium or tin plate aerosol can. Due to the separation of product and propellant, Bag-on-Valve can be used with compressed air or nitrogen at a pressure e.g. from 2 to 9 bar.

According to the invention, the composition is preferably used for the treatment of open wounds, preferably chronic wounds of humans and animals, wherein the use for the treatment of humans is preferred. The preferred use is by topical treatment of the wound(s) with the charged oxygen carrier(s) described.

Surprisingly it was found that it is possible to effectively treat open wounds with said charged oxygen carriers. As described above the healing of chronic wounds is often diminished due to the decreased oxygen supplement. It appears therefore logic that the treatment of the wounds requires the oxygen-charged oxygen carriers for treatment. However, according to the present invention it was found that it is possible to obtain a positive external wound healing by applying an oxygen-carrier charged with CO or NO. Without being bound our theory is that due to the oxygen partial pressure in air the ligand may be replaced by oxygen when applied to the wound and accordingly the wound healing is supported.

The composition of the present invention has the clear advantage of increased stability of the oxygen-carrier due to its non-oxidized status based on the charge with the CO or NO ligand resulting in a good preparation and storing stability. Further the composition is easy to apply and good to handle and provides a safe and effective approach to improve wound healing by facilitated diffusion mediated by the oxygen carrier/agent.

The composition of the present invention is applied externally. Depending on the state of the wound, it is applied on, preferably sprayed on the wound area in form of a fine spray.

According to the invention, it has been shown that open wounds, particularly also chronic wounds having very different causes, can be effectively treated. These can be wounds after operations, after trauma, after injuries, wounds with poor healing or hypoxic wounds, or also wounds caused by degenerative changes in the tissue. In this connection, they can be wounds caused by degenerative changes of the arterial blood vessels and wounds resulting from chronic venous insufficiency. These particularly include decubitus as well as chronic wounds, particularly those resulting from diabetes. Further wounds caused by burn (either by heat, by chemicals or by freezing) or by scalding can be effectively treated.

FIGURES

FIG. 1 shows the $O_2$ saturation curve of hemoglobin dependent from the $O_2$ surrounding partial pressure.

EXAMPLES

Example 1

Hemoglobin was isolated from whole blood of pigs by separating the red blood cells from serum, lysing the collected red blood cells, pelleting cell debris, charging the hemoglobin with CO by introducing CO gas until saturation of the liquid sample is obtained, heating the solution, carrying out several filtration steps, including a virus filtration step and washing the obtained hemoglobin solution by adding twice a 2-fold volume of 0.9% saline and filtering the solution.

A ready-to-use composition for wound treatment was prepared, comprising 10% of purified and stabilized hemoglobin, 0.05% N-acetyl cysteine and 0.7% phenoxy ethanol in 0.9% NaCl. The composition was charged again with CO gas, separated into 10 portions and packaged into an aerosol can, respectively.

Example 2

A first portion of the composition of Example 1 was used immediately after preparation to treat a female patient (Diagnosis: Diabetes, Hypertension) with a chronic wound at the right foot (7×2 cm). The wound was treated once daily by spraying the composition onto the wound. After 3 weeks first signs of healing were visible. The next weeks the healing process was pronounced and complete closing of the wound was obtained after 18 weeks.

Example 3

A second portion of the composition of Example 1 was stored at 4° C. for 2 years after preparation and thereafter used to treat a chronical wound of a male patient suffering from diabetes mellitus type II. The composition was applied to a chronic superficial ulcer (4×3 cm) at the left tibia of the patient. The wound was treated once daily. After two weeks a healing was appearing, after 4 weeks the wound was healed more than 50% of the baseline. The next weeks a fast healing was observed and complete closing of the wound was obtained after 8 weeks.

Example 4

A third portion of the composition of Example 1 was stored at 10° C. for 2 years. Thereafter it was used for treatment of a chronic superficial ulcer (4×2 cm) at the right leg of a male patient suffering from diabetes mellitus type II. The wound was treated once daily. After 2.5 weeks healing was visible. The next weeks a fast healing was observed and complete closing of the wound was obtained after 12 weeks.

Example 5

A portion of the composition of Example 1 was used to treat a male patient after contact with hot boiling water and steam. The diagnosis was $1^{st}$ and $2^{nd}$ degree burns on his face.

Initial treatment with cool gel and Neosporin for one week showed no improvement and by the tending physician the application of skin grafts on the nose and other parts of the face, like eyelids was proposed.

Instead the patient was treated with the composition of example 1 for 7 weeks. The composition was applied to the skin by spraying three or four times per day. A fast improvement and healing of the skin was observed and the patient was discharged from the hospital after seven weeks. No skin grafts were required.

Example 6: Comparison of Charged/Non-Charged Hemoglobin

A) A charged hemoglobin-spray was prepared according to Example 1

A ready-to-use composition for wound treatment was prepared, comprising 10% of purified and stabilized hemoglobin, 0.05% N-acetyl cysteine and 0.7% phenoxy ethanol in 0.9% NaCl. The composition was charged again with CO gas, separated into 20 portions and packaged into an aerosol can, respectively.

The composition can be stored between 4° C. and room temperature for months to years.

B) A second portion of the pig whole blood was treated as in Example 1 with the exception that no CO charging was carried out. During the heating step a considerable amount of hemoglobin precipitated. The following filtration steps were difficult to carry out. The yield of purified hemoglobin per liter whole blood decreased to less than 30% of the yield when the CO charging is carried out before heating. This shows that charging the samples with CO during preparation stabilizes the hemoglobin in a way that during a heating step considerably less hemoglobin precipitates.

A ready-to-use composition for wound treatment was prepared, comprising 10% of purified hemoglobin, 0.05% N-acetyl cysteine and 0.7% phenoxy ethanol in 0.9% NaCl. The composition was portioned and packaged into aerosol cans, respectively.

C) A further portion of hemoglobin was isolated from whole blood of pigs by a method as described in Example 1 of WO2003/077941 without charging the hemoglobin during preparation: the hemoglobin was freed from plasma and cellular membrane constituents without heating by means of centrifugation and ultrafiltration, and was purified.

A ready-to-use composition for wound treatment was prepared, comprising 10% of purified hemoglobin, 0.05% N-acetyl cysteine and 0.7% phenoxy ethanol in 0.9% NaCl. The composition was separated into 10 portions and packaged into an aerosol can, respectively.

A such prepared non-charged hemoglobin spray was freshly prepared during the treatment period as often as needed (all three days) and stored at 4° C. maximal for one day before use.

Treatment of Patients:

Several male patients (age 65-75) with Diabetic foot ulcer at the lower leg were treated for three months with hemoglobin spray according to A) (stored at 10° C. for up to 6 months) or a freshly prepared hemoglobin spray according to C) (storage at 4° C. for 3 days max., i.e. all three days a fresh composition was used) until complete wound healing was obtained at all of the patients. According to the attending dermatologists, the wound healing obtained with the compositions according to A) showed in all cases less secretion, less incrustation and/or less suppuration in comparison to wounds treated by the hemoglobin spray according to C) and in particular in comparison to wounds treated conventionally. Due to the minor problems the wounds treated with the charged hemoglobin composition according to A) showed a faster healing per cm² than the wounds treated with the non-charged hemoglobin spray C) and much faster than the conventionally treated wounds. The patients treated with composition A) furthermore reported less discomfort.

Example 7

Samples of compositions prepared according to Example 6A), Example 6B) or Example 6C), respectively, were examined considering the $O_2$ charge of the samples as well as the production of methemoglobin, a species which is unable to bind $O_2$. Furthermore methemoglobin affects hemoglobin molecules in the immediate vicinity in a way that these can still bind $O_2$, but cannot release it no more.

All the samples of Table 1 were diluted 1:1 with a 0.9% NaCl solution to imitate the conditions of a wound treatment. Samples 7.1 to 7.8 were measured immediately after dilution (storing of samples 7.5 to 7.8 was at room temperature before dilution). Gas treatment was as follows: 6 ml of said diluted solution were transferred into a 30 ml glass flask each. Gas treatment was carried out by filling the glass flask completely with the respective gas, closing the flask and pivoting the sample for 30 sec. All the samples were stored for the mentioned time period at 30° C. The samples were treated according to the conditions described in Table 1 and the total amount of hemoglobin (hemoglobin+methemoglobin), the oxygen content, the methemoglobin content and optionally the CO content was measured.

TABLE 1

| Example | sample | treatment | totalHb g/dL | $O_2$ % | CO % | MetHb % |
|---|---|---|---|---|---|---|
| 7.1 | Freshly prepared comp. according to Example 6A) | none | 5.5 | 1.7 | 96.3 | 3.9 |
| 7.2 | Freshly prepared comp. According to Example 6B) | none | 5.7 | 26.8 | | 5.1 |
| 7.3 | Freshly prepared comp. According to Example 6C) | none | 5.6 | 27.0 | | 4.7 |
| 7.4 | Composition of Example 6A), stored for 3 month (10° C.) | none | 5.9 | 1.8 | 96.5 | 3.8 |
| 7.5 | Composition of Example 7.2 | Stored for 24 h | 5.6 | 26.9 | | 11.2 |
| 7.6 | Composition of Example 7.2 | Stored for 48 h | 5.5 | 27.0 | | 17.0 |
| 7.7 | Composition of Example 7.3 | Stored for 24 h | 5.7 | 26.5 | | 10.5 |
| 7.8 | Composition of Example 7.3 | Stored for 48 h | 5.6 | 26.7 | | 16.2 |
| 7.9 | Composition of Example 7.4 | 0.5 h $O_2$ | 5.8 | 13.7 | 84.7 | 4.4 |
| 7.10 | Composition of Example 7.4 | 1 h $O_2$ | 5.7 | 19.6 | 79.1 | 4.2 |
| 7.11 | Composition of Example 7.4 | 2 h $O_2$ | 5.8 | 25.7 | 73.1 | 4.3 |
| 7.12 | Composition of Example 7.4 | 3 h $O_2$ | 5.9 | 30.7 | 68.1 | 4.2 |
| 7.13 | Composition of Example 7.4 | 24 h $O_2$ | 5.7 | 33.5 | 59.6 | 9.8 |
| 7.14 | Composition of Example 7.4 | 48 h $O_2$ | 5.8 | 32.5 | 55.9 | 15.5 |
| 7.15 | Composition of Example 7.4 | 72 h $O_2$ | 5.7 | 31.7 | 55.8 | 16.0 |
| 7.16 | Composition of Example 7.4 | 0.5 h $CO_2$ | 5.8 | 4.0 | 91.8 | 5.7 |
| 7.17 | Composition of Example 7.4 | 1 h $CO_2$ | 5.7 | 6.0 | 90.0 | 5.7 |
| 7.18 | Composition of Example 7.4 | 2 h $CO_2$ | 5.9 | 9.2 | 86.7 | 5.8 |
| 7.19 | Composition of Example 7.4 | 3 h $CO_2$ | 5.7 | 9.6 | 85.1 | 6.9 |
| 7.20 | Composition of Example 7.4 | 24 h $CO_2$ | 5.6 | 4.9 | 77.5 | 19.7 |
| 7.21 | Composition of Example 7.4 | 48 h $CO_2$ | 5.8 | 8.2 | 68.2 | 27.4 |
| 7.22 | Composition of Example 7.4 | 72 h $CO_2$ | 5.7 | 9.4 | 65.9 | 28.3 |
| 7.23 | Composition of Example 7.4 | 0.5 h air | 5.8 | 9.2 | 89.0 | 4.5 |
| 7.24 | Composition of Example 7.4 | 1 h air | 5.7 | 12.4 | 85.9 | 4.4 |
| 7.25 | Composition of Example 7.4 | 2 h air | 5.9 | 18.0 | 80.5 | 4.3 |
| 7.26 | Composition of Example 7.4 | 3 h air | 5.6 | 20.7 | 77.9 | 4.3 |
| 7.27 | Composition of Example 7.4 | 24 h air | 5.8 | 24.3 | 69.3 | 9.1 |
| 7.28 | Composition of Example 7.4 | 48 h air | 5.7 | 25.4 | 64.3 | 13.9 |
| 7.29 | Composition of Example 7.4 | 72 h air | 5.7 | 26.8 | 62.2 | 14.3 |

As can be seen from the results in Table 1 the compositions of the invention, wherein the oxygen carrier is charged with CO, not only can be stored for a long time without forming methemoglobin, but further are able to replace the bound CO by $O_2$ when it is offered to the charged oxygen carrier. If exposed to 100% $O_2$ (examples 7.9 to 7.15) the $O_2$ saturation of the hemoglobin increases very fast.

If the composition is exposed to $CO_2$, representing the situation inside of mammalian pathway-active tissue, an increased amount of methemoglobin is formed (examples 7.16 to 7.22).

The $O_2$ partial pressure in air is only about 21%, thus according to the $O_2$ saturation curve of hemoglobin shown in FIG. 1, the maximum possible $O_2$ saturation of hemoglobin with oxygen under air is about 29%. Considering Examples 7.23 to 7.29 the surprising result is that within 3 hours the composition exposed to air is charged with 20.7% oxygen, but still has a very low methemoglobin content. When external wounds are treated, the composition is sprayed to the (cleaned) wound surface and remains in contact with air.

These results show that a composition according to the invention comprises a stabilized oxygen carrier which after several months of storing provides high oxygen transport when it is in contact with air.

What is claimed is:

1. A method for the external treatment of an open wound surface, comprising spraying on the open wound surface an aqueous composition comprising:
   (a) an oxygen carrier, wherein al least 40% of oxygen binding sites of said oxygen carrier are charged by a non-$O_2$ ligand, such that the oxygen carrier is sprayed on the open wound surface with the oxygen carrier in its non-oxidized state in the spray and provides availability of oxygen to the open wound surface in the presence of oxygen partial pressure in air as opposed to a pressurized chamber of pure oxygen, and
   (b) at least one further ingredient selected from the group consisting of electrolyte(s), preservative(s), stabilizer(s), anti-flocculant(s), anticoagulant(s), pH buffering agent(s), solvent(s), antioxidant(s), film-forming agent(s) and crosslinking agent(s), wherein the oxygen carrier is hemoglobin and the non-$O_2$ ligand is carbon monoxide (CO).

2. The method according to claim 1, wherein the wounds to be treated are selected from the group consisting of chronic wounds, operation wounds, injury wounds, wounds after trauma, open wounds, wounds with poor healing, hypoxic wounds, wounds arising from degeneration or stenosis of arterial blood vessels, diabetic wounds, chronic venous insufficiency wounds, decubitus ulcer wounds, burn wounds, chemical burns, freezing burns, and scalding wounds.

3. The method according to claim 1, wherein the composition administered is an organic solution.

4. The method according to claim 1, wherein at least 50% of the oxygen carrier is provided in non-$O_2$ ligand-charged form.

5. The method according to claim 4, wherein at least 60% of the oxygen carrier is provided in non-$O_2$ ligand-charged form.

6. The method according to claim 5, wherein at least 70% of the oxygen carrier is provided in non-$O_2$ ligand-charged form.

7. The method according to claim 6, wherein at least 80% of the oxygen carrier is provided in non-$O_2$ ligand-charged form.

8. The method according to claim 7, wherein at least 90% of the oxygen carrier is provided in non-$O_2$ ligand-charged form.

9. The method according to claim 1, wherein the oxygen carrier is naturally occurring hemoglobin of human or animal origin.

10. The method according to claim 1, wherein the oxygen carrier is artificially-treated, crosslinked hemoglobin.

11. The method according to claim 1, wherein the composition administered is provided in sterilized form.

12. The method according to claim 1, wherein the composition administered is provided in an aerosol can.

13. The method according to claim 12, wherein the composition administered is provided in a pressure pack aerosol can.

14. The method of claim 1, wherein the ligand is replaced by oxygen when the spray is applied to the open wound surface due to oxygen partial pressure in the air.

15. A method for the external treatment of an open wound surface, comprising spraying from an aerosol on the open wound surface an aqueous composition comprising:
   (a) a hemoglobin oxygen carrier, wherein at least 40% of oxygen binding sites of the hemoglobin oxygen carrier are charged by carbon monoxide to render the hemoglobin oxygen carrier in a non-oxidized/non-activated status, such that the oxygen carrier is sprayed on the open wound surface with the oxygen carrier in its non-oxidized state in the spray and provides availability of oxygen to the open wound surface in the presence of oxygen partial pressure in air as opposed to a pressurized chamber of pure oxygen, and
   (b) at least one further ingredient selected from the group consisting of electrolyte(s), preservative(s), stabilizer(s), anti-flocculant(s), anticoagulant(s), pH buffering agent(s), solvent(s), antioxidant(s), film-forming agent(s) and crosslinking agent(s).

* * * * *